United States Patent [19]

Lambowitz

[11] Patent Number: 4,486,533

[45] Date of Patent: Dec. 4, 1984

[54] FILAMENTOUS FUNGI FUNCTIONAL REPLICATING EXTRACHROMOSOMAL ELEMENT

[75] Inventor: Alan M. Lambowitz, St. Louis, Mo.

[73] Assignee: St. Louis University, St. Louis, Mo.

[21] Appl. No.: 460,684

[22] Filed: Jan. 24, 1983

Related U.S. Application Data

[63] Continuation-in-part of Ser. No. 414,131, Sep. 2, 1982, abandoned, which is a continuation-in-part of Ser. No. 395,884, Jul. 7, 1982, abandoned.

[51] Int. Cl.³ .................... C12N 15/00; C12N 1/14; C12N 1/00; C12P 21/00; C12P 21/02; C12P 19/34

[52] U.S. Cl. .................. 435/172.3; 435/68; 435/70; 435/91; 435/254; 435/317; 935/24; 935/68; 935/72; 935/73

[58] Field of Search .............. 435/68, 70, 91, 172, 435/254, 317; 536/27

[56] References Cited

PUBLICATIONS

Lambowitz et al.: J. Bacteriology 108, 1087 (1971).
Stohl et al.: Nucl. Acids Res. 10, 1439 (1982).
Collins et al.: Cell 443 (1981).
Stahl et al.: Molec. Gen. Genet. 178, 639 (1980).
Zakian: Proc. Natl. Acad. Sci. USA 78, 3128 (1981).

*Primary Examiner*—Thomas Wiseman
*Assistant Examiner*—James Martinell
*Attorney, Agent, or Firm*—Bertram I. Rowland

[57] ABSTRACT

A functional extrachromosomal element capable of replication in filamentous fungi is provided. The extrachromosomal element employs (1) a mitochondrial replicating element or (2) a lower organism replication sequence recognized by the fungus, in combination with foreign DNA to provide replication, transcription, and translation of foreign regulatory elements and genes. The extrachromosomal element is exemplified by a mitochondrial replicating system from Neurospora.

The cell strain *E. coli* HB101 containing the plasmid pALS-1-1 has been deposited at the A.T.C.C. on July 13, 1982, for patent purposes and given the designation ATCC 39157.

The cell strain *E. coli* HB101 containing the plasmid pALS-2 has been deposited at the A.T.C.C. on July 13, 1982, for patent purposes and given the designation ATCC 39158.

9 Claims, 2 Drawing Figures

FILAMENTOUS FUNGI FUNCTIONAL REPLICATING EXTRACHROMOSOMAL ELEMENT

CROSS-REFERENCE TO RELATED APPLICATIONS

This application is a continuation-in-part patent application of pending prior application, U.S. Ser. No. 414,131, filed Sept. 2, 1982, now abandoned, which is a continuation-in-part patent application of pending prior application, U.S. Ser. No. 395,884, filed July 7, 1982, now abandoned.

BACKGROUND OF THE INVENTION

1. Field of the Invention

Since the demonstration that a wide variety of genes expressing proteins from prokaryotes and eukaryotes could be introduced into foreign hosts and expressed, there have been continuing efforts to expand the capabilities and efficiencies with which the proteins can be produced and isolated. The efficiency with which a particular protein may be obtained will vary greatly depending on a wide variety of factors.

While the code for translating from RNA to amino acid is substantially universal, as a practical matter codons may be more or less efficiently translated depending upon the host. Depending upon the ratios of tRNAs, genes may be translated with varying efficiencies into the desired protein. To the extent that the host is more closely related to the source of the gene, it is anticipated that the gene will be more efficiently translated. Also, alien regulatory signals controlling the transcription and translation of the gene may be useful, avoiding the need to substitute the host regulatory signals for the regulatory signals of the gene source.

Also of interest is whether leader peptides will be recognized by the host to secrete the proteins of interest. Particularly desirable is where the leader peptide which is naturally present is recognized by the host, so that the need for introducing a synthetic leader is not required. However, the ability to obtain secretion of the desired peptide is not the most important factor and this will vary from host to host.

Also of interest is the nature of the products that the host or other species related to the host produces. In this situation, one can expect that by taking a gene from a related source and introducing it into an expression host, the product will be efficiently produced. Particularly for non-proteinaceous products where a useful host lacks only one or two enzymes in the metabolic sequence for production of the desired product, these enzymes could be introduced into the desired host to provide the desired product.

Another consideration is the ability to grow the host commercially, it being desirable that the same or similar host have been the previous subject of commercial fermentation processes.

2. Brief Description of the Prior Art

Stohl, et al., Nucleic Acids Res. (1982) 10: 1439-1458 describes the characterization of two plasmid DNAs found in mitochondria of wild-type *Neurospora intermedia* strains. Collins, et al., Cell (1981) 24:443-452 describes the characterization of a novel plasmid found in mitochondria *N. crassa*. Case, et al., PNAS USA (1979) 76:5259-5263 describes the efficient transformation of *N. crassa* by utilizing hybrid plasmid DNA. Hymen, et al., PNAS USA (1982) 79:1578-1582 and Zakian, ibid (1981) 78:3128-3132 describes the use of mitochondrial DNA for high-frequency transformation for yeast. Stahl, et al., PNAS USA (1982) 79:3641-3645 have reported experiments with Podospora employing a hybrid plasmid consisting of *E. coli* plasmid pBR325 and defective mtDNA expressing the senescence traits.

SUMMARY OF THE INVENTION

Novel stable extrachromosomal autonomously replicating DNA vectors are provided for filamentous fungi. Particularly, mitochondrial plasmid DNA is isolated and used as a stably replicating vector or a prokaryotic replication system, particularly in combination with a structural gene recognized by the host, is employed as a stably replicating vector. Desirably, the mitochondrial plasmid DNA is joined to another replicating system to provide a shuttle vector to enhance the convenience of genetic manipulation. Foreign DNA capable of expression may be introduced into the constructs employing the stably replicating vector and used for transformation of filamentous fungi to provide for the production of desired products.

DESCRIPTION OF THE SPECIFIC EMBODIMENTS

Figure 1:
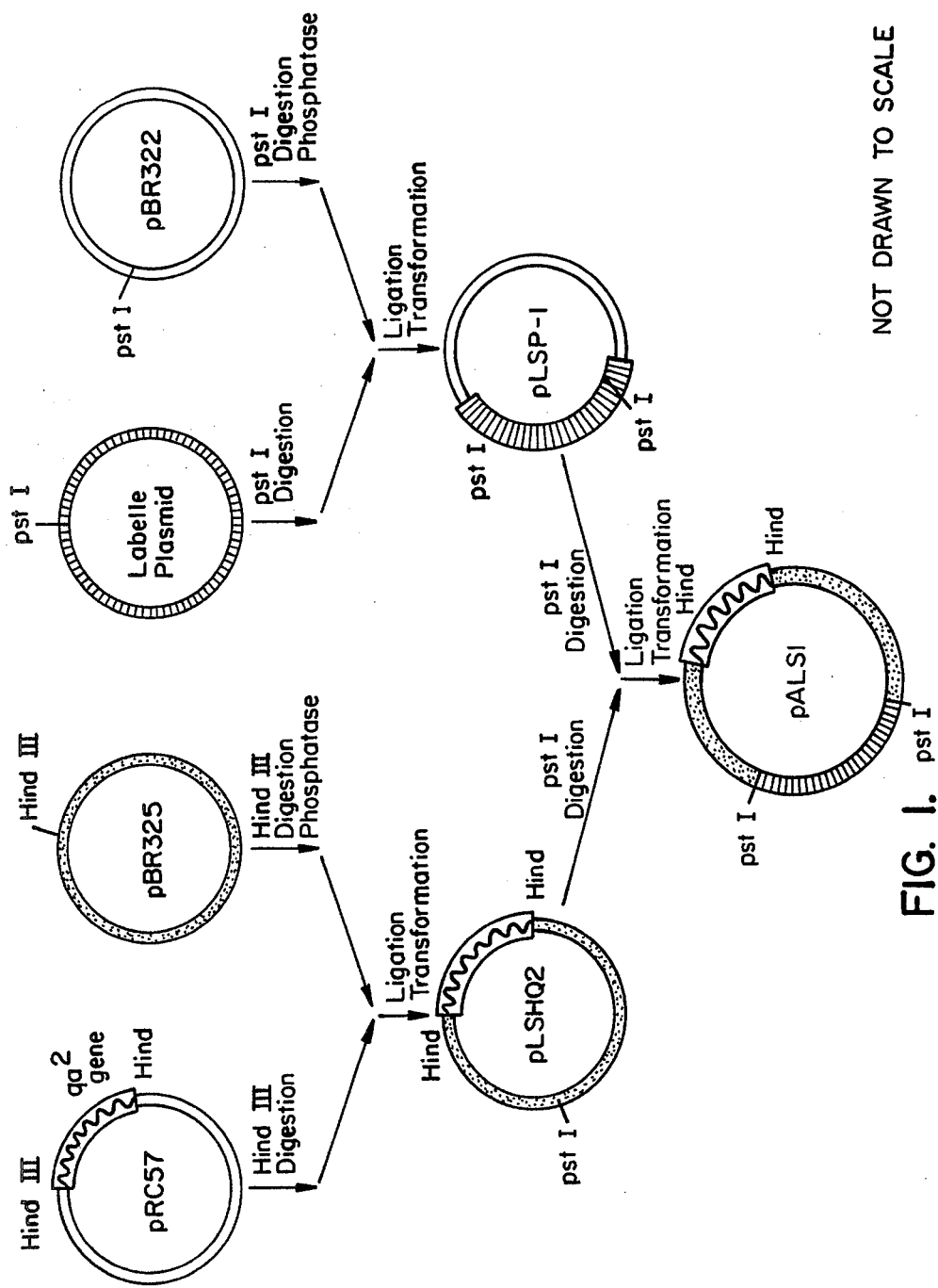
FIG. 1 is a schematic of the preparation of pALS-1.
Figure 2:
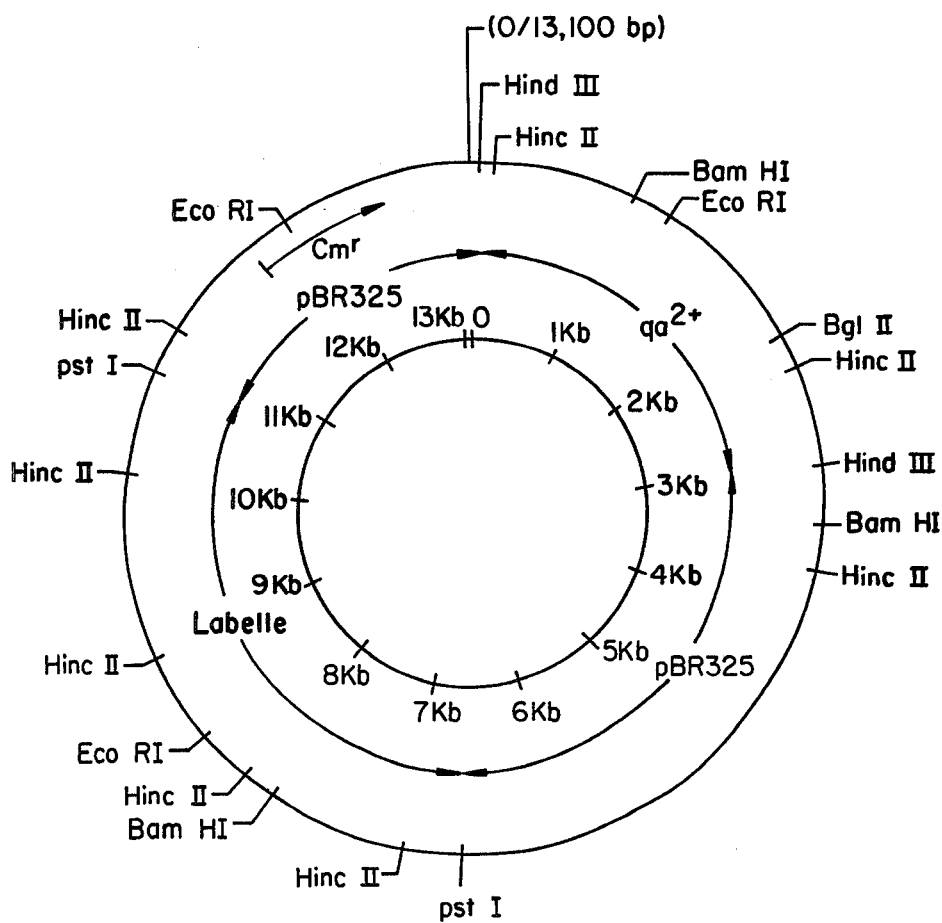
FIG. 2 is a restriction map of the pALS-1.

In accordance with the subject invention, novel vectors, constructs employing the vectors, and filamentous fungi containing episomal elements are provided. Two different vectors are provided: (1) A eukaryotic replication system derived from filamentous fungal mitochondrial plasmid DNA; (2) a prokaryotic replication sequence in combination with a structural gene from a filamentous fungus, which gene is reconized by its fungal host.

For the eukaryotic vector, mitochondrial plasmid DNA is isolated from filamentous fungi to provide autonomously replicating constructs in a filamentous fungal host. In performing the method of the subject invention, a particular strain of filamentous fungus is grown and the mitochondria isolated by conventional techniques (Lambowitz, Methods Enzymol (1979) 59:421-423). Closed circular plasmid DNA is then obtained from mitochondrial lysates by conventional means, for example, by centrifugation directly in CsCl-ethidium bromide gradients. (Collins, et al., supra). Closed circular plasmid mtDNA may then be restricted into one or more fragments and the fragments inserted into an appropriate vector for cloning. The resulting plasmids provide shuttle vectors for use for further manipulation, for introduction of other DNA, for replication, transcription and translation in filamentous fungi, as well as for production of non-proteinaceous products. Alternatively, the replicating DNA segment from the filamentous fungi may be isolated from the cloning vector and used in conjunction with other DNA to provide for cloning and expression vectors. In addition, by employing homologous DNA sequences, integration of the plasmid or portion thereof can be facilitated.

The subject host and source of the mitochondrial plasmid DNA are the filamentous fungi, particularly the class Ascomycetes. This class includes such representative genera as Neurospora, Aspergillus and Penicillium.

Particular species include *N. intermedia, N. crassa*, etc. This class is distinguished by having the ascus, a saclike structure containing sexual spores (ascospores).

The autonomously replicating segment which provides for the stability of the extrachromosomal element upon introduction into Ascomycetes host is obtained from mitochondrial plasmid DNA. Thus, strains of ascomycetes are screened for the presence of such plasmids by isolating low molecular weight plasmids, generally less than about 10 kb, from mitochondria. The mitochondrial replicon should be one which is capable of initiating replication outside of the mitochondrion. The plasmid serving as the source of the mitochondrial replicon may also be found in the cytosol. Therefore, preferred sources of the replicon of this invention are those strains which have a plasmid primarily located in the mitochondrion, but also appearing in the cytosol. The isolated plasmid DNA may then be linearized or further restricted and cloned in an appropriate vector, normally a prokaryotic vector. Particularly, vectors for *E. coli*, e.g., pBR322, *Bacillus subtilis*, or a variety of Gram negative bacteria, e.g., pRK290, are available.

It is found that when a shuttle vector construct is employed containing the filamentous fungal replication system, a prokaryotic replication system and a structural gene which permits selection in a filamentous fungal host after passaging, constructs can be isolated devoid of the mitochondrial replication system. While these constructs can be stably maintained in a filamentous fungal host, they are found to have a lower efficiency of transformation. Particularly, a replication system in an *E. coli* plasmid in combination with a filamentous fungal marker is found to be stably replicated in filamentous fungi. An illustrative marker is qa-2.

By preparing shuttle vectors employing the filamentous fungal replication system in conjunction with prokaryotic replication systems or lower eukaryotic replication systems, e.g. yeast, the heterologous replication systems may be screened for competence in filamentous fungi.

The replication system may be derived from any source which provides for stable maintenance in the lower organism host. Such replication systems may come from episomal elements, chromosomes, plastid DNA, or viruses (phage).

Conveniently, a vector may be chosen which has one or more desired restriction sites for insertion of the linearized mitochondrial plasmid DNA which has been isolated. Vectors are normally chosen which provide for selection so that upon transformation of a host, the transformants may be preferentially selected. The cloned DNA may then be isolated and the mitochondrial plasmid DNA excised from the vector as desired. Conveniently the same restriction enzyme which was employed for introduction of the mitochondrial plasmid DNA may be used for excision of the mitochondrial plasmid DNA. However, the mitochondrial plasmid DNA which provides the autonomously replicating segment when joined to the prokaryotic vector provides a convenient shuttle vector to allow for ease of further manipulation and introduction of other DNA segments. Thus, for the most part, the prokaryotic cloning vector will be retained at this stage, even for a construct ultimately having only the filamentous fungal replication system or intended to retain such system.

In order to aid in selecting for the DNA construct which has the autonomously replicating segment for the filamentous fungi, it is initially desirable to introduce a basis for selection of the presence of such segment in the construct. The marker employed as the basis for selection may be widely varied. An auxotrophic host may be employed and the DNA segment which is introduced would have a marker that provides prototrophy to the host. Thus, by employing a medium lacking the requisite nutrient for the parent host, only transformants will be able to grow in the selective nutrient medium. Other markers may also be employed, such as resistance to a variety of cytotoxic agents, e.g., metal ions, etc. Alternatively, a marker may be introduced to provide for viral immunity. The particular choice of marker is not a critical aspect of this invention, and any marker may be employed which provides the desired selectivity. The filamentous fungi may then be grown under selective conditions which allows for expansion of the transformed host.

The resulting marker containing shuttle vector may now be used for insertion of a wide variety of DNA segments, which DNA is normally foreign to the host. For expression, various regulatory signals may be introduced into the vector, either as part of a foreign gene or separate from the foreign gene. Of particular importance are promoters recognized by the host which provide for efficient transcription. Also, in many cases, various regulatory signals may be employed for regulating the promoter. Naturally occurring feedback mechanisms may be employed by appropriate selection of promoters involved in metabolism or catabolism in the filamentous fungal host. Other promoters may be employed which are regulated by the growth stage of the host, such as vegetative growth, conidia formation, etc. The choice of promoter and regulatory means will vary with a particular product, the desired manner of isolation, and its intended function in the host.

The genes which are introduced may provide for a wide variety of products ranging from single amino acids to high molecular weight polypeptides. In addition, the genes may provide for production of enzymes which modify non-proteinaceous products, such as antibiotics. Polypeptide products of interest include a variety of prokaryotic or eukaryotic enzymes, mammalian hormones, toxins, vaccines and the like.

In addition to the promoter as a regulatory signal, and the DNA associated with regulation of the promoter, other regulatory signals include terminators, usually paired to the promoter, ribosomal start sites, sequences coding for leader peptides, sequences capable of amplifying the gene of interest by reiteration etc. Amplifying genes and their promoters, include the genes for DHFR, metallothionein, etc.

While an order has been indicated for preparation of the DNA constructs according to this invention, any order may be used which is convenient, based on ability to clone and select for the fragments, availability of restriction sites, and availability of combinations of regulatory signals and genes. With each construct one or more strategies may be developed. The subject vectors are characterized by being capable of being stably maintained extrachromosomally in a filamentous fungal host, e.g. an ascomycete host. Thus, the fungal host may be grown through a plurality of generations, for example, for ascomycetes, involved with conidia formation, or be maintained in vegetative growth, while maintaining the subject vectors as independent entities. The subject vectors are further found to be capable of replication outside of the mitochondria, particularly in the cytosol or nucleus. The subject vectors from the mitochondrial plasmid DNA can be reisolated from the host and used for further manipulation or transformation. In addition, the vectors may be modified by removal of prokaryotic or eukaryotic segments other than the autonomously replicating segments, so as to reduce the size of the vector.

As already indicated vectors can be prepared having as its only replication system, a system from a lower order microorganism, particularly prokaryotic. These vectors can be readily obtained by employing shuttle vectors containing a selective marker for transformation of filamentous fungi, where one replication system is other than from the filamentous fungi and the other replication system is derived from the filamentous fungi.

The construct is used to transform a filamentous fungal host at high efficiency and the resulting transformants may then be grown one or more generations and the plasmid DNA isolated from the fungal host. The smaller plasmid DNA which lacks the filamentous fungal replication system, but is capable of replication in filamentous fungi, can be used as a shuttle vector and can be modified by introduction of structural genes for expression in the filamentous fungi.

The following examples are offered by way of illustration and not by way of limitation.

EXPERIMENTAL

Materials and Methods

Strains of Neurospora and Growth Conditions

The *N. crassa* strain used as the recipient for transformation experiments was M246-89601-2A (obtained from Dr. Mary Case, University of Georgia, Athens). This strain is a derivative of wild-type 74A which contains a stable qa-2 mutation (M246), an arom-9 mutation (M6-11), and an inos (89601) mutation. The double mutant qa-2, arom-9, lacks both the biosynthetic and catabolic dehydroquinase activities and is unable to grow on minimal medium without a supplement of aromatic amino acids.

Standard procedures were used for the maintenance of strains and preparation of conidia (Davis and de Serres, Methods Enzymol (1971) 17A:79-141). Mycelia were grown in liquid cultures for 14 h (25°) as described (Lambowitz et al., J. Cell Biol. (1979) 82:17-31). The recipient strain was grown in either Vogel's or Fries minimal medium supplemented with phe, tyr, and trp (each 80 $\mu$g per ml); PABA (2 $\mu$g per ml); and inositol (0.2 mg per ml). Transformants were maintained on Vogel's minimal medium supplemented with inositol (0.2 mg per ml).

Transformation of Neurospora

Transformation of Neurospora was carried out as described by Case et al. (Proc. Natl. Acad. Sci. USA (1979) 76:5259-5263) with modifications (Schweizer et al., ibid (1981) 78:5086-5090).

Recombinant Plasmid DNAs

The construction of plasmid pALS-1 is outlined schematically in FIG. 1. Plasmid pRC57 was obtained from Dr. Mary Case, University of Georgia, Athens, Ga. (pRC57 is reported as equivalent to pVC57, described in Alton et al., Gene (1978) 4:241-259; Schweizer, et al., PNAS USA (1981) 78:5086-5090). The plasmid contains the Neurospora qa-2+ gene cloned into the single HindIII-site of *E. coli* plasmid pBR322. Plasmid pLSHQ2 was constructed by recloning the qa-2 gene excised with HindIII from pRC57 in *E. coli* plasmid pBR325 using standard procedures. Plasmid pLSP-I was constructed by linearizing the mitochondrial plasmid from P405-Labelle by digestion with PstI. The 4.1 kb PstI-fragment was then cloned into the single PstI-site of pBR322 (Stohl et al., 1982, supra). Plasmid pALS-1 was constructed by recloning the 4.1 kb Labelle DNA sequence from pLSP-1 into the PstI site of plasmid pLSHQ2. The structure of pALS-1 was verified by restriction enzyme mapping.

Restriction Enzyme Analysis

Restriction enzymes were obtained from New England Biolabs (Beverly, Mass.) and Bethesda Research Laboratories (Gaithersburg, Md.). DNA was digested using reaction conditions specified by the suppliers. Restriction fragments were analyzed on horizontal slab gels containing 0.7 to 1.2% agarose, as previously described (Stohl et al., Nucl. Acids Res. (1982) 10:1439-1458). For preparative purposes, restriction digests were separated on gels containing low melting point agarose (Bethesda Research Laboratories, Gaithersburg, Md.) and DNA was extracted from the gels as described by the suppliers.

Southern Hybridizations

DNA gel patterns were transferred to nitrocellulose strips (Schleicher and Schuell, BA85) as described by Southern, J. Mol. Biol. (1975) 98:503-517. DNA fragments to be used as probes were labeled by nick translation (Rigby et al., J. Mol. Biol. (1977) 113:237-251) using $^{32}$P-ATP or $^{32}$P-CTP (ca. 1000 Ci per mmole; New England Nuclear, Boston Mass.). Hybridization conditions were as described (Collins et al., Cell (1981) 24:443-452), except that strips containing DNA from subcellular fractions were hybridized for 40 to 48 h, instead of 18 to 24 h.

Analysis of Neurospora Transformants by Colony Filter Hybridization

The procedure developed for Neurospora colony filter hybridization is an adaptation of established procedures for bacteria (Grunstein and Hogness, PNAS USA (1976) 72:3961-3965) and yeast (Hinnen et al., ibid (1978) 75:1929-1933). Nitrocellulose filters (Schleicher and Schuell, BA85circles) were washed (two times; one hour each wash) at 60° in Westergaard's sorbose plating medium and laid over agar plates containing the same medium. A loopful of a conidial suspension was spotted on the filter and incubated at 30° for one to three days until colonies formed. The filters were then placed on 3 layers of Whatman 3 MM paper saturated with a solution containing 50 mM EDTA, pH 8.0, 2.5% 2-mercapto ethanol or 50 mM EDTA, 20 mM DTT, pH 8.0, for 15 to 30 min., then transferred to Petri dishes containing three layers of Whatman 3 MM paper saturated with 2 mg per ml Zymolyase (60,000 units per g, Kirin Brewery, Japan or 5,000, units per g, Seikagaku Co., Ltd from Miles Laboratories, Inc.) in 20 mM phosphate buffer, pH 7.0, and incubated for 3 to 4 h at 37°. Two to three times during the incubation, a small drop of zymolyase solution was placed on each of the individual colonies. After the incubation, the colonies were lysed by placing the filters on Whatman 3 MM paper saturated with a solution containing 1.5 M NaCl, 0.1 M NaOH for 2 to 3 min. The filters were then transferred to a 9 cm Whatman filter on a Buchner filtering unit and strong suction was applied for 2 to 3 min. The filters were washed three times with 50 ml of a solution containing 0.3 M NaCl, 0.03 M sodium citrate, and 0.2 M Tris-HCl, pH 7.5. The filters were air dried briefly and baked under vacuum at 75° for 1 h. The filters were prewashed in 0.5% SDS, 2X SSC (37°) for 5 to 12 h, followed by two 15 min. rinses in 2X SSC (room temperature). Filters were prehybridized in a solution containing 5X SSC, 1X Denhardt's solution, 0.5% SDS, 1.7 mg per ml calf thymus DNA in glass petri dishes at 67° to 68° for 12 to 18 h. Strips were hybridized with $^{32}$P-labeled DNA fragments (1 to $3 \times 10^{6}$ cpm) in a fresh solution of the same buffer for 18 to 24 h at 67° to 68°. The DNA probes had been $^{32}$P-labeled by nick translation. After hybridization, the filters were washed once with 2X SSC for 15 min., then 3X(1 hr each) with 1 X SSC, 0.5% SDS, 60°. Filters were blotted, air dried, wrapped in Saran wrap and autoradiographed at 70° with a Dupont Intensifying Screen.

The recipient strain, *N. crassa* M246-89601-2A, was transformed with pALS-1 or with pRC57 or pLSHQ2, the latter two contain the qa-2+ gene cloned in pBR322 or pBR325, respectively. The transformation frequencies for pALS-1 were 140 and 151 transformants per μg DNA compared with 8 and 18 for pRC57 and pLSHQ2, respectively.

Transformants were selected and analyzed by colony filter hybridization to determine whether they contained sequences from pBR325. DNA isolated from nuclear and cytosolic fractions of each transformant was digested with either EcoRI or PstI+HindIII and Southern blots were hybridized with pALS-1 which had been $^{32}$P-labeled by nick translation. A similar analysis was carried out for the untransformed recipient strain. The untransformed recipient showed a single strong band due to the defective qa-2 gene along with weaker bands. This pattern of hybridization is similar to that reported previously (Alton et al., Gene (1978) 4:241-259; Case et al., (1979), supra).

Each of five transformants gave a series of bands. Some of these corresponded to bands in pALS-1 whereas others did not. The strong hybridizations suggest that plasmid DNAs are located in the nuclear and/or cytosolic fractions. Southern hybridizations showed that there may be some plasmid DNA in purified mitochondrial fractions, but the concentration is low compared to the concentration of mtDNA.

Six transformants were grown under non-selective conditions through a number of generations and then plated on minimal medium plus inositol to test for the presence of qa-2+ gene. All showed some loss of the qa-2+. For individual transformants the proportion of progeny remaining qa-2+, after 3 conidial passes ranged from less than 0.01% to 65%. The results suggest that the qa-2+ gene is not stably integrated into chromosomal DNA. The results do not exclude the possibility that transformants contain integrated in addition to free plasmid.

To determine whether the pALS-1 transformants contain free plasmid DNA, DNA was isolated and used to transform *E. coli* strain HB101 with selection for the chloramphenicol-resistance marker contained on the pBR325 portion of the plasmid. DNAs from 10 of 14 pALS-1 transformants gave chloramphenicol-resistant colonies whereas DNA isolated from the untransformed recipient strain gave no such colonies. Plasmid DNAs were isolated from the *E. coli* transformants by the mini-prep procedure and analyzed by digestion with EcoRI and PstI+HindIII. The gel patterns and subsequent restriction mapping and hybridization experiments showed that the tranformants contained two different plasmids. The smaller form, designated pALS-2, was found in 20 *E. coli* transformants and the larger form, pALS-1-1 was found in 2 *E. coli* transformants.

Two of the Neurospora transformants gave both types of plasmid.

Physical maps of pALS-1-1 and pALS-2 were constructed by restriction enzyme digestion and Southern hybridization. pALS-1-1 is identical to pALS-1 by these criteria. The plasmid is renamed pALS-1-1 to indicate that it has experienced "one pass" through a Neurospora host during which it may have acquired modifications which facilitate autonomous replication.

pALS-2 contains the Neurospora qa-2+ gene and most or all of the pBR325 sequences including the chloramphenicol-resistance gene, as judged by restriction enzyme mapping, Southern hybridizations, and ability to transform these markers. Most of the Labelle mitochondrial plasmid sequences are missing, as is the pBR325 PstI-site at which the Labelle plasmid was originally inserted. pALS-2 may retain some Labelle plasmid sequences, but it appears that all of the Labelle sequences are missing. The most likely interpretation is that pALS-2 was formed by deletion of at least the majority of Labelle sequences from pALS-2 in the Neurospora tranformants. The occurrence of the same deletion in different Neurospora transformants would suggest some specific recombination process. The presence of pALS-2 accounts for some of the novel bands detected in the Southern hybridizations of the Neurospora transformants.

Next, the transformation of the original Neurospora recipient strain with pALS-1-1 and pALS-2 was repeated to provide pALS-1-2 and pALS-2-1. Transformation frequencies were 380 and 160 transformants per μg DNA again compared to 8 and 18 μg for plasmids pRC57 and pLSHQ2 which transform mainly by integration. For Neurospora transformed with pALS-1-1, 10 of 24 gave unmodified pALS-1-1 and 14 of 24 gave the deleted form, pALS-2. For Neurospora transformed with pALS-2, 3 of 3 give unmodified pALS-2. The proportion of Neurospora transformants giving unmodified pALS-1-1 is considerably higher than in either of two separate experiments using pALS-1 (2/22 and 1/13). This suggests that there may be "conditioning" with passage through Neurospora so that the plasmid is either more stable or replicates more efficiently. Cell fractionation and Southern hybridization experiments are consistent with a nuclear/cytosolic location of the pALS-1-1 and pALS-2.

The results show that the pALS-1 recombinant plasmid can transform Neurospora qa-2− strains at high frequency. The plasmid appears to be autonomously replicating as judged by recovery of unmodified plasmid DNA from the transformants after extended vegetative growth. The phenotypic characteristics of the transformants (i.e., very low proportion of abortive transformants) and loss of the qa-2+ gene with growth under nonselective conditions are also consistent with autonomous replication. In addition to pALS-1, the initial Neurospora transformants also contained a modified form, designated pALS-2, in which most or all of the Labelle mitochondrial plasmid sequences have been deleted. The retransformation experiments suggest that pALS-2 may also be capable of autonomous replication in Neurospora. The results do not exclude the possibility that some proportion of the plasmid DNAs are also integrated and in fact certain novel bands detected in Southern hybridizations of DNAs from transformants and the finding that in some transformants the plasmid is not lost completely with growth under non-selective conditions are consistent with this idea.

The fact that the qa-2+ gene is expressed in transformants indicates that the functional gene is located in the nuclear and/or cytosolic compartments as opposed to the mitochondria. The apparatus used for gene expression in Neurospora mitochondria is markedly different from that in the nucleus and cytosol, including the use of a modified genetic code (Heckman et al., PNAS USA (1980) 77:3159-3163). The mitochondrial genetic apparatus would not be expected to accurately express a nuclear gene. The nuclear/cytosolic location of the pALS plasmids is supported by the cell fractionation experiments. However, the results do not exclude the possibility that some proportion of the plasmid is present in purified mitochondria.

pALS-1 and pALS-2 contain the *E. coli* R factor derived chloramphenicol resistance gene ($cam^R$), which encodes chloramphenical acetyltransferase and which can be expressed in yeast (Cohen et al. Proc. Natl. Acad. Sci. USA (1980) 77:1078-1082). Neurospora transformants were plated on Westergaard's sorbose plating medium containing 3.5 mg/ml chloramphenicol. In order to inhibit Neurospora alternate oxidase and increase sensitivity to chloramphenical, 150 $\mu$g/ml salicyl hydroxamic acid (SHAM) were added. Two strains transformed with pALS1-1 appeared to be chloramphenicol resistant as judged by the presence of colonies having greater diameter than the host strain or another wild type (74A), suggesting expression of the *E. coli* $cam^R$ gene in the Neurospora transformants,.

A derivative of pALS-1-2 was prepared as follows. A HindIII/AvaI fragment from the Tn5 insertion in pBR322 carrying the $kan^R$ gene was blunt ended at its AvaI site and was cloned into the HindIII/PvuII site of pBR322. The Labelle fragment was excised from pALS-1-2 with PstI, blunt ended as before, and cloned into the blunt ended EcoRI site of the pBR322-$kan^R$ plasmid prepared above to provide the plasmid pBR322-$kan^R$-Labelle. This plasmid was opened with HindIII and the qa-2 fragment obtained by digestion of pALS-1-2 with HindIII inserted into the HindIII site to provide the pALS-1-2 derivative.

A parallel derivative of pALS-2 was constructed as follows. First, pALS-2 was restricted with BglII and PvuII, blunt ended with S1 nuclease, and religated, thereby deleting the BglII/PvuII region containing nonessential sequences. Next, this derivative was linearized with ClaI, blunt ended, and cut with HindIII to receive the HindIII/blunt ended AvaI fragment containing the $kan^R$ gene, described above.

Neurospora strain M246-89601-2A was transformed with derivatives of pALS-1-2 and pALS-2 containing the Neurospora qa-2+ gene and the *E. coli* kanamycin-resistance gene from Tn5. Neurospora transformants were selected for resistance to antibiotic G418 (600 $\mu$g per ml). The pALS-1-2 derivative gave 55 to 65 transformants per $\mu$g DNA, nearly all of which could be subcultured. Subsequent screening shown 75% of the transformants were qa-2+. The pALS-2 derivative gave 16 to 25 $G418^R$ transformants per $\mu$g DNA. Subsequent screening showed that all of these were qa-2+. When qa-2+ transformants were selected, both plasmids gave at least five times more transformants per $\mu$g DNA. All that were tested could be subcultured and 25 to 50% were subsequently found to be G418-resistant. The results suggest that the G418-resistance gene (*E. coli* $kan^R$ contributed by the plasmids is expressed in Neurospora.

pALS-1 and pALS-2 and their derivatives may be modified in a variety of ways for use as amplification and expression vectors. Regulatory signals recognized by the host filamentous fungi may be obtained from chromosomal or mitochondrial sources and inserted into the above vectors. Various wild-type genes may be isolated and used as a source of the transcriptional and translational regulatory signal to produce fused or unfused proteins, to provide for leader peptides and to permit regulated or constitutive production of the desired peptide product. As illustrative, the qa-2 gene may be restricted and the desired gene introduced, so as to be under the control of the qa-2 promoter and provide for a fused protein. Alternatively, an exonuclease, e.g. BAL31, may be employed for removing various numbers of base pairs to provide vectors where the inserted gene may be in an appropriate juxtaposition to the ribosomal binding site of the qa-2 gene. Further, qa-2 may be sequenced and a unique restriction site inserted by in vitro mutagenesis to provide for insertion at the desired site. Conveniently, the f-met codon can serve as the focal point for insertion, employing linkers or oligonucleotides to provide for the necessary base pairs in the vicinity of the ribosomal binding site.

The subject invention provides a vector which may be stably maintained in filamentous fungi, particularly Neurospora. Thus, the genes of filamentous fungi may now be cloned and genes readily detected by employing auxotrophic hosts. By selecting for prototrophic transformants, sequences providing for the desired genes may be isolated in this manner. Also, the associated regulatory function may be isolated for use with foreign genes.

The results demonstrate plasmids capable of autonomously replicating in filamentous fungi and capable of continued segregation with hyphal tips so as to be stably maintained during vegetative growth. While it is not certain that their stable maintenance is as a result of a specific segregation mechanism or a very efficient replication origin which generates a sufficiently high copy number for the plasmid, the latter would appear to be the more likely explanation. Based on the subject results, mitochondrial replication origins have found use in constructing autonomously replicating vectors for filamentous fungi.

While the above provides a full and complete disclosure of the preferred embodiments of the invention, various modifications, alternate constructions, and equivalents may be employed without departing from the true spirit and scope of the invention. Therefore, the above description and illustrations should not be construed as limiting the scope of the invention which is defined by the appended claims.

What is claimed is:

1. A method for producing autonomously replicating vectors for use in Neurospora which comprises:
   isolating mitochondria having autonomously replicating plasmid DNAs from Neurospora;
   linearizing said plasmid DNAs and inserting said plasmid DNAs into a cloning vector to produce a hybrid cloning plasmid and introducing said hybrid cloning plasmid into an amplifying host to provide a modified host;
   growing said modified host for said cloning vector to clone said mitochondrial plasmid DNA and isolating said hybrid cloning plasmids;
   introducing at least a portion of said cloning plasmid containing at least a portion of said linearized mitochondrial plasmid into a Neurospora and selecting for a Neurospora in which said portion is stably maintained outside of the mitochondria.

2. A method according to claim 1, wherein said portion of said linearized mitochondrial plasmid is joined to at least one marker recognized by a Neurospora.

3. An extrachromosomal hybrid DNA derived at least in part from mitochondrial plasmid DNA from a Neurospora said extrachromosomal hybrid DNA being capable of stable extrachromosomal maintenance outside of the mitochondria in a Neurospora host.

4. Hybrid DNA comprising a plasmid having a prokaryotic replication sequence and a replication sequence derived from Neurospora mitochondrial plasmid DNA, wherein said hybrid DNA is capable of stable maintenance outside of the mitochondria as an extrachromosomal element in Neurospora.

5. Hybrid DNA according to claim 4 including a marker capable of selection in a Neurospora.

6. Hybrid DNA according to claim 4 including a gene expressing a protein foreign to a Neurospora.

7. A Neurospora containing a hybrid DNA according to claim 4 and capable of stable replication as an extrachromosomal element in said Neurospora.

8. A host according to claim 7, wherein said prokaryotic replication sequence is from *E. coli*.

9. A host according to either of claims 7, or 10, wherein said plasmid includes a marker capable of selection in said Neurospora and a structural gene foreign to said Neurospora.

* * * * *